US009675259B2

United States Patent
Lee et al.

(10) Patent No.: US 9,675,259 B2
(45) Date of Patent: Jun. 13, 2017

(54) PHYSIOLOGICAL FUNCTION DETECTING EARPHONE AND DETECTING METHOD THEREOF

(71) Applicant: Cheng Uei Precision Industry Co., Ltd., New Taipei (TW)

(72) Inventors: James Cheng Lee, New Taipei (TW); Kuo Yang Wu, New Taipei (TW); Bor Kuan Lu, New Taipei (TW); Wen Shung Hu, New Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 558 days.

(21) Appl. No.: 14/205,737

(22) Filed: Mar. 12, 2014

(65) Prior Publication Data

US 2015/0257662 A1    Sep. 17, 2015

(51) Int. Cl.
| | | |
|---|---|---|
| *A61B 5/02* | (2006.01) | |
| *A61B 5/024* | (2006.01) | |
| *H04R 1/10* | (2006.01) | |
| *A61B 5/00* | (2006.01) | |
| *A61B 5/1455* | (2006.01) | |

(52) U.S. Cl.
CPC ...... *A61B 5/02427* (2013.01); *A61B 5/02405* (2013.01); *A61B 5/6803* (2013.01); *A61B 5/7207* (2013.01); *H04R 1/1091* (2013.01); *A61B 5/14552* (2013.01); *A61B 5/746* (2013.01); *H04R 2430/00* (2013.01); *H04R 2499/10* (2013.01)

(58) Field of Classification Search
CPC .............. A61B 5/02427; A61B 5/7207; A61B 5/02405; A61B 5/6803; A61B 5/14552; A61B 5/746; H04R 1/1091; H04R 2499/10; H04R 2430/00
See application file for complete search history.

(56) References Cited

U.S. PATENT DOCUMENTS

| | | | | |
|---|---|---|---|---|
| 5,673,692 A | * | 10/1997 | Schulze | A61B 5/14552 356/41 |
| 2010/0217102 A1 | * | 8/2010 | LeBoeuf | A61B 5/00 600/310 |
| 2012/0203077 A1 | * | 8/2012 | He | A61B 5/02055 600/301 |
| 2015/0011898 A1 | * | 1/2015 | Romesburg | A61B 5/02416 600/479 |

* cited by examiner

*Primary Examiner* — Michael Kahelin
*Assistant Examiner* — Tho Tran
(74) *Attorney, Agent, or Firm* — Lin & Associates Intellectual Property, Inc.

(57) ABSTRACT

A physiological function detecting earphone includes an earphone body, an earplug mounted at one side of the earphone body and defining a window, a light processing module including a light sensing module towards the window, and a signal processing module. A detecting method using the earphone by a participant includes the steps of: the participant inserts the earplug in the ear canal thereof; the light sensing module senses the changes of light emitted through the window and then reflected by the wall of the ear canal; the light processing module processes the reflected light changes to get photoplethysmography (PPG) signals; and the signal processing module receives and processes the PPG signals to get physiological information of the participant.

13 Claims, 6 Drawing Sheets

PHYSIOLOGICAL FUNCTION DETECTING EARPHONE AND DETECTING METHOD THEREOF

BACKGROUND OF THE INVENTION

1. Field of the Invention

The present invention relates to an earphone, and more particularly to a physiological function detecting earphone and a detecting method thereof.

2. The Related Art

The autonomic nervous system (ANS) is the part of the peripheral nervous system that acts as a control system, functioning largely below the level of consciousness, and controls visceral functions. The ANS affects heart rate, blood pressure, mood changes, life stress and so on. Therefore, if a person can early detect his autonomic nervous variation, personal health can be paid attention as early as possible to prevent individual physiological or psychological disease. Heart rate variability (HRV) is commonly used to show the ANS of variation in the time interval between heartbeats. Methods used to detect beats include: ECG, blood pressure, ballistocardiograms and the pulse wave signal derived from the photoplethysmography (PPG).

A traditional physiological function detecting earphone for detecting the heart rate variability (HRV) includes an earphone body, a light source and a light sensor. The earphone body has an earplug made of pervious to light material. In use, the earplug of the earphone body is inserted into the ear canal of a participant, then light emitted by the light source penetrates through the earplug and is reflected by the wall of the ear canal, and last the light sensor senses the reflected light changes in a period of time to get photoplethysmography (PPG) signals so as to detect the HRV.

However, manufacturing material of the earplug has an effect on transmittance of light through the earplug. Furthermore, the earphone is apt to move in the ear canal along with the shaking of the participant, so that will easily cause an interspace between the earplug and the wall of the ear canal. As a result, the light outside the ear canal can go into the ear canal through the interspace so that will affect the PPG signals got by the light sensor and ultimately affect the accuracy of the HRV.

Therefore, a physiological function detecting earphone capable of overcoming the abovementioned problems is required.

SUMMARY OF THE INVENTION

An object of the present invention is to provide a physiological function detecting earphone which includes an earphone body, an earplug mounted at one side of the earphone body, a light processing module and a signal processing module. At least one window is opened through the earplug. The light processing module includes an inner ring spacer, at least one light sensing module disposed on one end face of the inner ring spacer and facing to the window of the earplug, a signal amplifier and an analog-to-digital (A/D) converter which are disposed on the inner ring spacer and coupled with the light sensing module. The light sensing module includes a visible light source for emitting at least one wavelength of light through the window of the earplug, and a light sensor for sensing reflected light changes by the wall of the ear canal of a participant. The signal amplifier and the A/D converter process the reflected light changes to get PPG signals. The signal processing module is coupled with the signal amplifier and the A/D converter via the inner ring spacer for receiving and processing the PPG signals to get physiological information of the participant.

Another object of the present invention is to provide a detecting method of the physiological function detecting earphone. The detecting method includes the steps: the participant inserts the earplug of the physiological function detecting earphone in the ear canal thereof; the light sensor senses the changes of light which is emitted by the visible light source through the window and then reflected by the wall of the ear canal of the participant; the signal amplifier and the A/D converter process the reflected light changes to get the PPG signals; and the signal processing module receives and processes the PPG signals to get physiological information of the participant.

As described above, the physiological function detecting earphone utilizes the window opened in the earplug to gather the light in a narrow area of the ear canal of the participant so as to reduce the effect of the manufacturing material on the transmittance of light. So the physiological function detecting earphone can effectively improve the accuracy of the PPG signals and the physiological information of the participant.

BRIEF DESCRIPTION OF THE DRAWINGS

The present invention will be apparent to those skilled in the art by reading the following description thereof, with reference to the attached drawings, in which.

DETAILED DESCRIPTION OF THE EMBODIMENT

Figure 1:
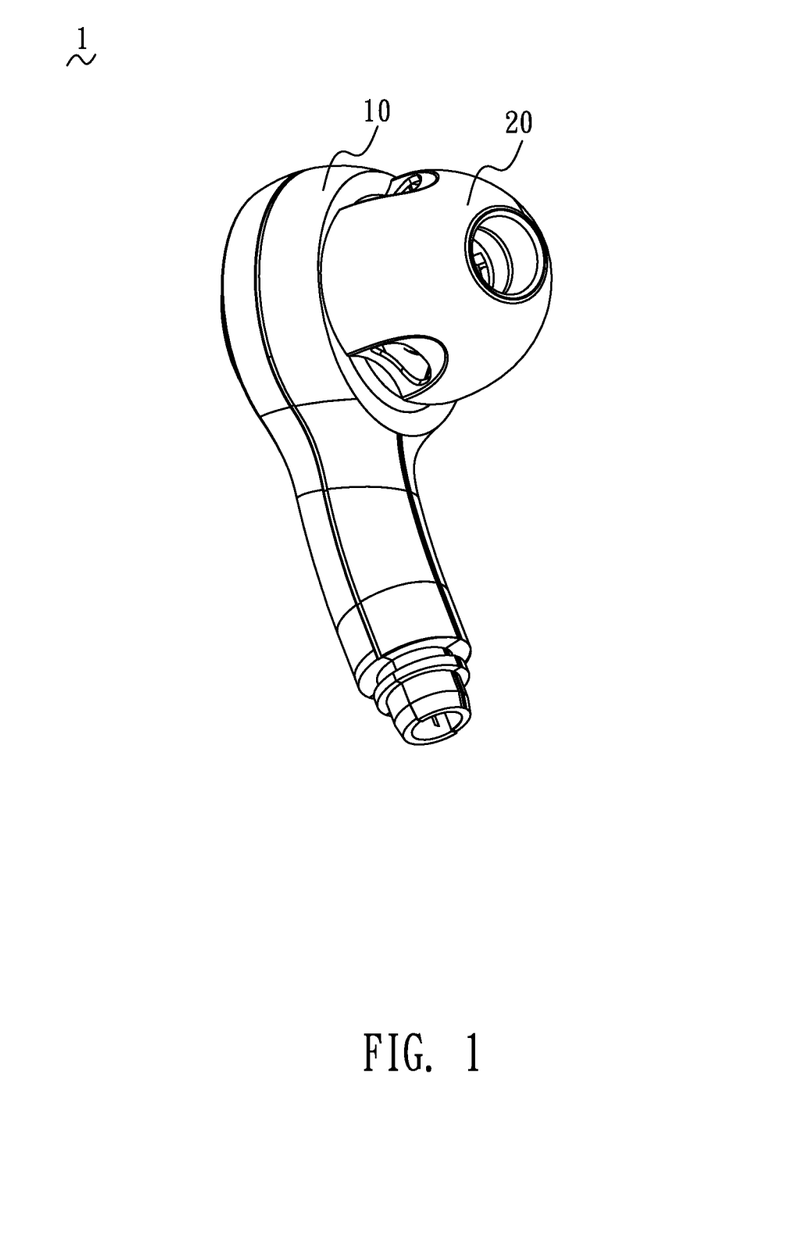
FIG. 1 is a perspective view of a physiological function detecting earphone according to an embodiment of the present invention.
Figure 2:
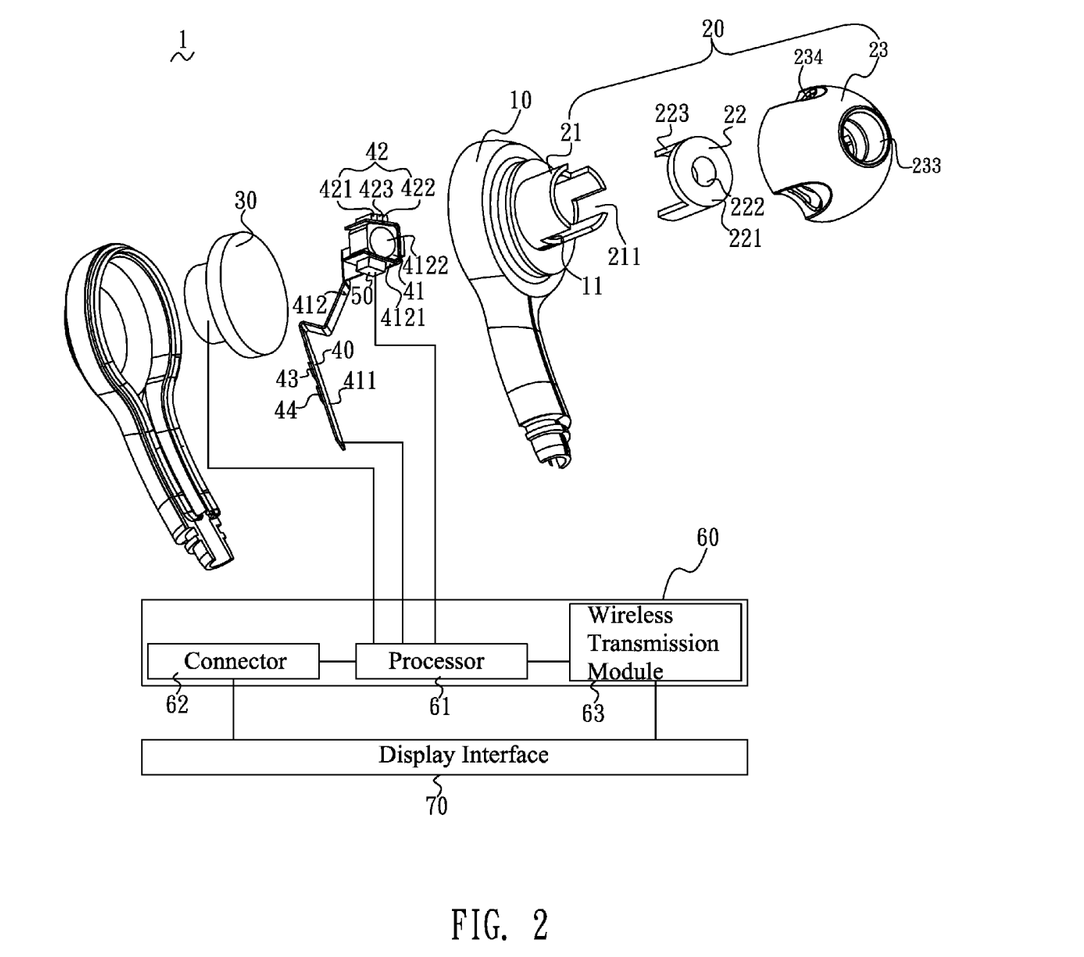
FIG. 2 is an exploded view of the physiological function detecting earphone of FIG. 1.

Referring to FIG. 1 and FIG. 2, a physiological function detecting earphone 1 according to an embodiment of the present invention includes an earphone body 10, an inserting body 20, a loudspeaker 30, a light processing module 40, an accelerometer 50 and a signal processing module 60.

One side of the earphone body 10 defines a first sound hole 11. The inserting body 20 is mounted at the one side of the earphone body 10 and is used to be inserted into the ear canal of a participant. The inserting body 20 includes a holder 21, a holding frame 22 and an earplug 23. The holder 21 is substantially of cylindric shape and is formed by the circumferentia of the first sound hole 11 perpendicularly extending sideward. At least one opening 211 is opened through the inside, the outside and the free edge of the holder 21.

The holding frame 22 has a discoid cover board 221 covering the end mouth of the holder 21. The periphery of the cover board 221 perpendicularly extends to form at least one inserting board 223 made of pervious to light material and inserted in the opening 211 of the holder 21. In practice, the cover board 221 can be made of lightproof material.

Figure 4:
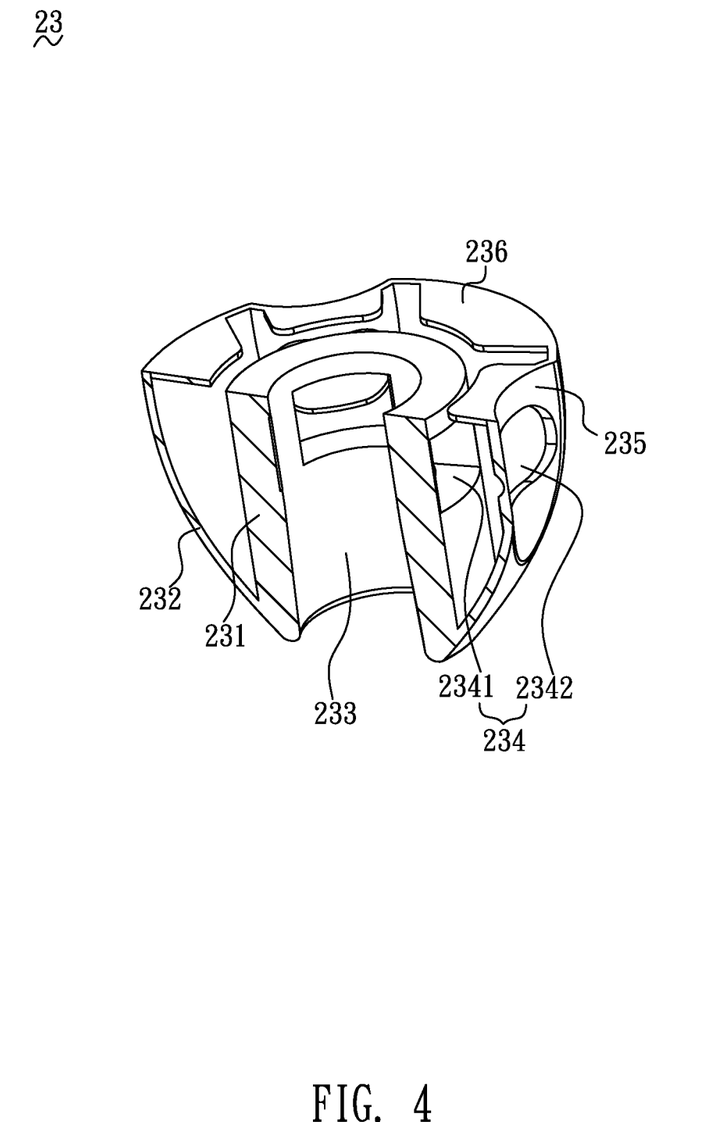
FIG. 4 is a sectional view of an earplug of the physiological function detecting earphone of FIG. 2.

Referring to FIG. 1, FIG. 2 and FIG. 4, the earplug 23 is made of lightproof material and has a cylindric sleeve 231 worn around the holder 21 and the holding frame 22. The outer edge of the sleeve 231 extends towards the earphone body 10 to form a substantial bowl-shaped guiding portion 232. At least one window 234 is opened through the earplug 23. In detail, the window 234 includes a first window 2341 and a second window 2342 which are opened in the sleeve 231 and the guiding portion 232 respectively and are in alignment with each other. The earplug 23 is mounted outside the holder 21 and the holding frame 22 with the inserting board 223 being exposed through the window 234. The outside of the guiding portion 232 is partly concaved inward to form a groove 235 around the second window 2342 for deforming the guiding portion 232 easily. The free edge of the guiding portion 232 perpendicularly protrudes inward to form a light blocking eave 236. The sleeve 231 and the light blocking eave 236 abut against the one side of the earphone body 10 for blocking the light outside the ear canal of the participant.

Figure 3:
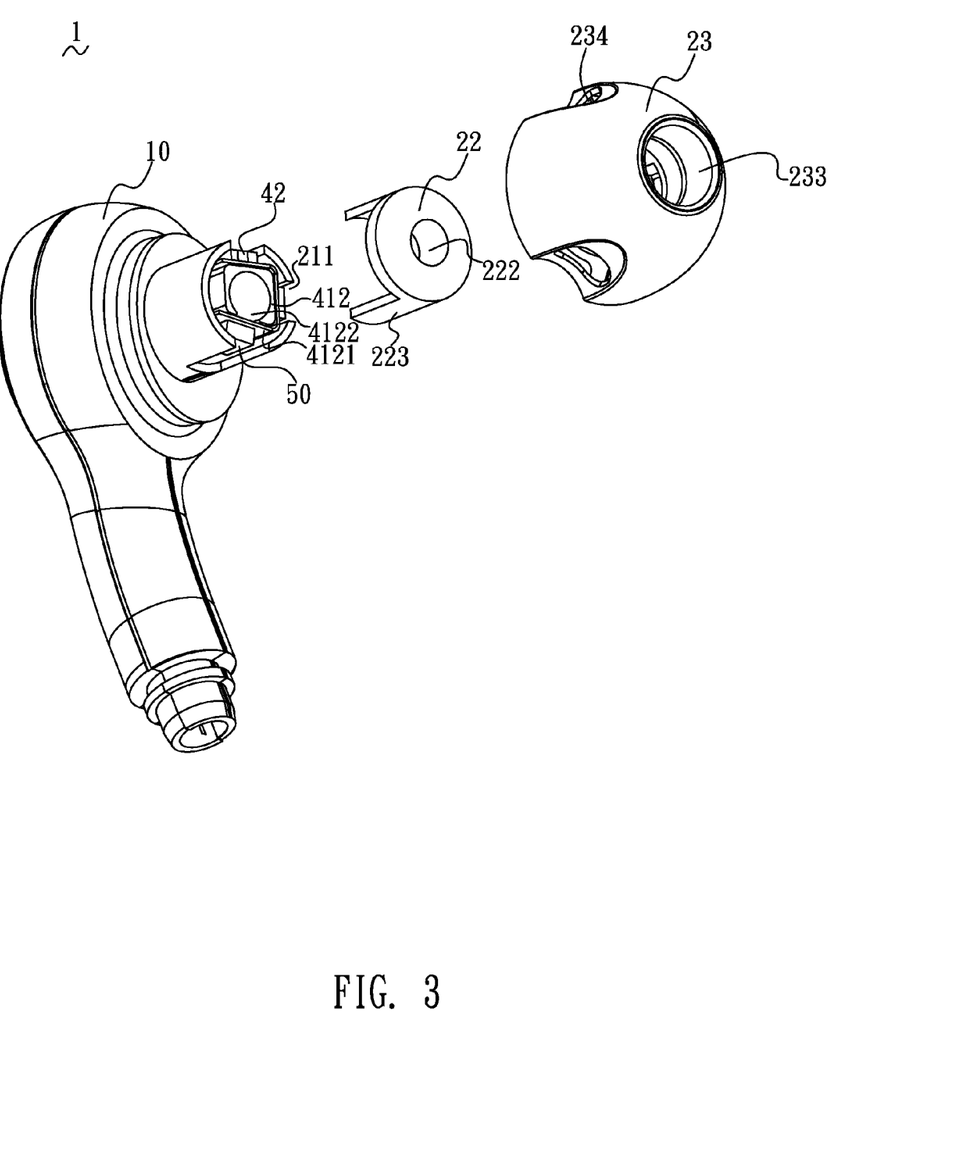
FIG. 3 is a partly exploded view of the physiological function detecting earphone of FIG. 1.

Referring to FIG. 2 and FIG. 3, the light processing module 40 includes an inner ring spacer 41, at least one light sensing module 42 disposed on one end face of the inner ring spacer 41 and facing to the window 234 of the earplug 23, a signal amplifier 43 and an A/D converter 44 which are disposed on the inner ring spacer 41 and coupled with the light sensing module 42. In detail, the light sensing module 42 together with a part of the inner ring spacer 41 are located in the holder 21 and face to the inserting board 223 of the holding frame 22. The light sensing module 42 includes a visible light source 421 for emitting at least one wavelength of light through the inserting board 223 of the holding frame 22 and the window 234 of the earplug 23, and a light sensor 423 for sensing reflected light changes by the wall of the ear canal of the participant. The signal amplifier 43 and the A/D converter 44 process the reflected light changes to get PPG signals.

In detail, the inner ring spacer 41 includes a flexible printed circuit (FPC) board 411 and a connecting frame 412 connected with one end of the FPC board 411. The FPC board 411 is positioned in the earphone body 10 and the connecting frame 412 is positioned in the holder 21 of the inserting body 20. The connecting frame 412 defines at least one fitting surface 4121 facing to the inserting board 223 of the holding frame 22 and the window 234 of the earplug 23. The light sensing module 42 is disposed on the fitting surface 4121, and the signal amplifier 43 and the A/D converter 44 are disposed on the FPC board 411.

Referring to FIG. 2, the signal processing module 60 is coupled with the signal amplifier 43 and the A/D converter 44 via the inner ring spacer 41 for receiving and processing the PPG signals to get physiological information of the participant. In detail, the signal processing module 60 includes a processor 61 and a wireless transmission module 63. The processor 61 receives the PPG signals and change cycle of the PPG signals and further works out the time interval of each change cycle. Then the processor 61 describes a continuous variation of waveform and records physiological status of the participant by the HRV analytical method. The wireless transmission module 63 transmits the continuous variation of waveform and the physiological status of the participant to a display interface 70. The physiological status includes PPG curve chart, heart rate, HRV, degree of blood oxygen saturation and so on. The signal processing module 60 further includes at least one connector 62 capable of transmitting the continuous variation of waveform and the physiological status of the participant to the display interface 70.

The display interface 70 can be a portable electronic product, such as a smart phone and a smart watch. According to the physiological information provided by the physiological function detecting earphone 1, the display interface 70 can instantly change the types of music to make the music change along with the physiological status of the participant.

Referring to FIG. 2 again, the light sensing module 42 further includes an invisible light source 422 disposed in one place with the visible light source 421 and the light sensor 423. Preferably, the visible light source 421 emits red light at a wavelength of about 610~700 nanometers which is more easily reflected by blood to get better signal contrast. According to the characteristics of the invisible light source 422, degree of blood oxygen saturation can be worked out by comparing reflected signals from the invisible light source 422 with the reflected light from the visible light source 421. It is worth mentioning that the invisible light source 422 can be omitted when monitoring the heart rate and the HRV.

Referring to FIG. 2 again, the physiological function detecting earphone 1 further includes an accelerometer 50 disposed on another end face of the inner ring spacer 41 and facing to another window 234 of the earplug 23. In detail, the accelerometer 50 is disposed on another fitting surface 4121 of the connecting frame 412 of the inner ring spacer 41 and faces to the inserting board 223 of the holding frame 22 and the window 234 of the earplug 23. The accelerometer 50 is coupled with the signal processing module 60 for continuously transmitting displacement information to the signal processing module 60 in use. Then the signal processing module 60 judges work start point of the light sensing module 42 and controls on-off states of the light sensing module 42 according to the displacement information so as to capture appropriate ranges from the PPG signals and further get the physiological information of the participant.

In this invention, the window 234 of the earplug 23 and the accelerometer 50 can effectively eliminate transmittance of light error caused by the manufacturing material of the earplug 23 and the shaking of the participant. Furthermore, the physiological function detecting earphone 1 can monitor sleep states of the participant by means of the accelerometer 50 and the light sensing module 42. So, the physiological function detecting earphone 1 can be further used in patients with sleep apnea so as to send an alarm in case of symptoms.

Referring to FIG. 2 and FIG. 3, the cover board 221 of the holding frame 22 defines a second sound hole 222 penetrating through a middle part thereof. A third sound hole 233 is circled by the sleeve 231 of the earplug 23 and penetrates through the sleeve 231. The connecting frame 412 of the inner ring spacer 41 defines a fourth sound hole 4122. The first sound hole 11, the second sound hole 222, the third sound hole 233 and the fourth sound hole 4122 are in alignment with one another to form a sound track, and the fourth sound hole 4122 is aligned between the first sound hole 11 and the second sound hole 222. The loudspeaker 30 is positioned in the earphone body 10 and faces to the first, fourth, second and third sound holes 11, 4122, 222 and 233.

Figure 5:
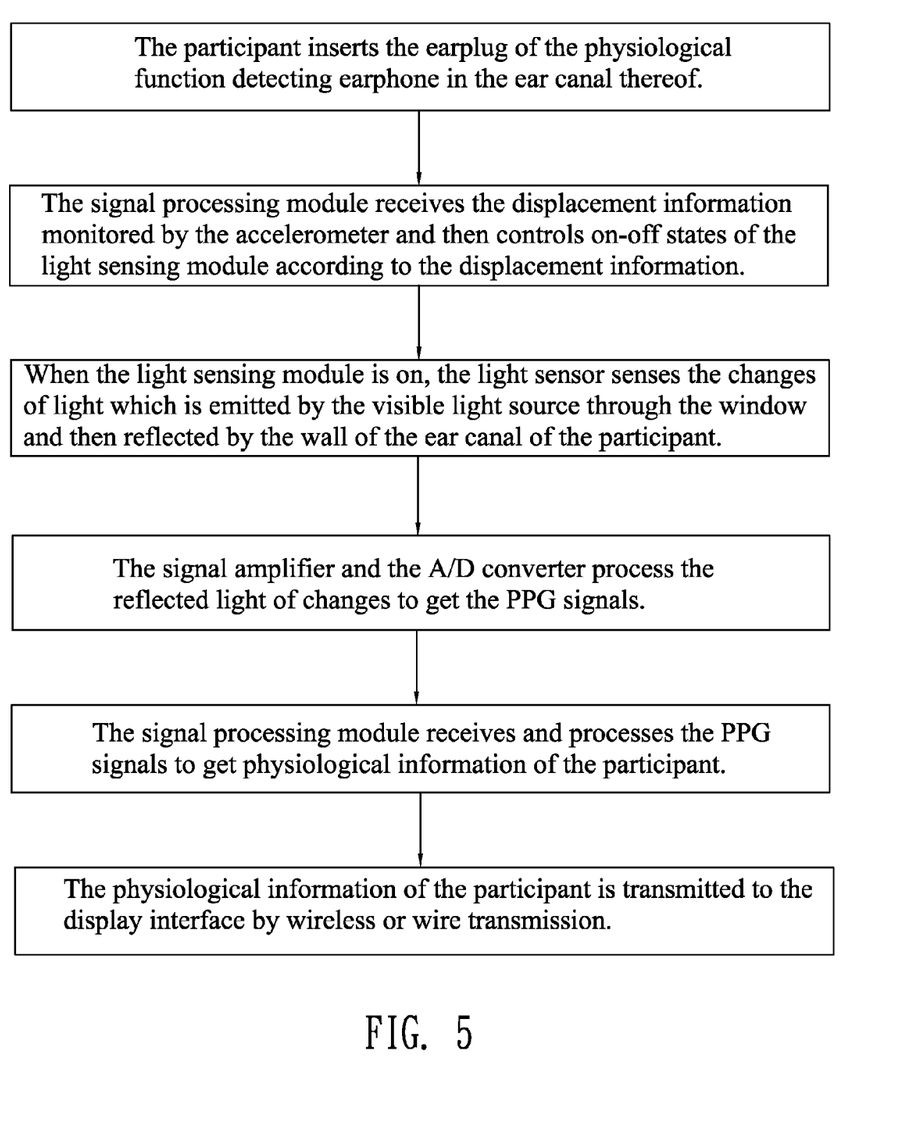
FIG. 5 and FIG. 6 are flow diagrams showing two detecting methods of the physiological function detecting earphone of FIG. 1.

Referring to FIG. 2 and FIG. 5, a detecting method of the physiological function detecting earphone 1 includes the following steps.

Step 1: the participant inserts the earplug 23 of the physiological function detecting earphone 1 in the ear canal thereof.

Step 2: the signal processing module 60 receives the displacement information monitored by the accelerometer 50 and then controls on-off states of the light sensing module 42 according to the displacement information.

Step 3: when the light sensing module 42 is on, the light sensor 423 senses the changes of light which is emitted by the visible light source 421 through the window 234 and then reflected by the wall of the ear canal of the participant.

Step 4: the signal amplifier 43 and the A/D converter 44 process the reflected light changes to get the PPG signals.

Step 5: the signal processing module 60 receives and processes the PPG signals to get physiological information of the participant.

Step 6: the physiological information of the participant is transmitted to the display interface 70 by wireless or wire transmission.

In other embodiments, the light sensing module 42 can keep being on. The signal processing module 60 directly captures appropriate ranges from the PPG signals to get physiological information of the participant according to the displacement information.

Figure 6:
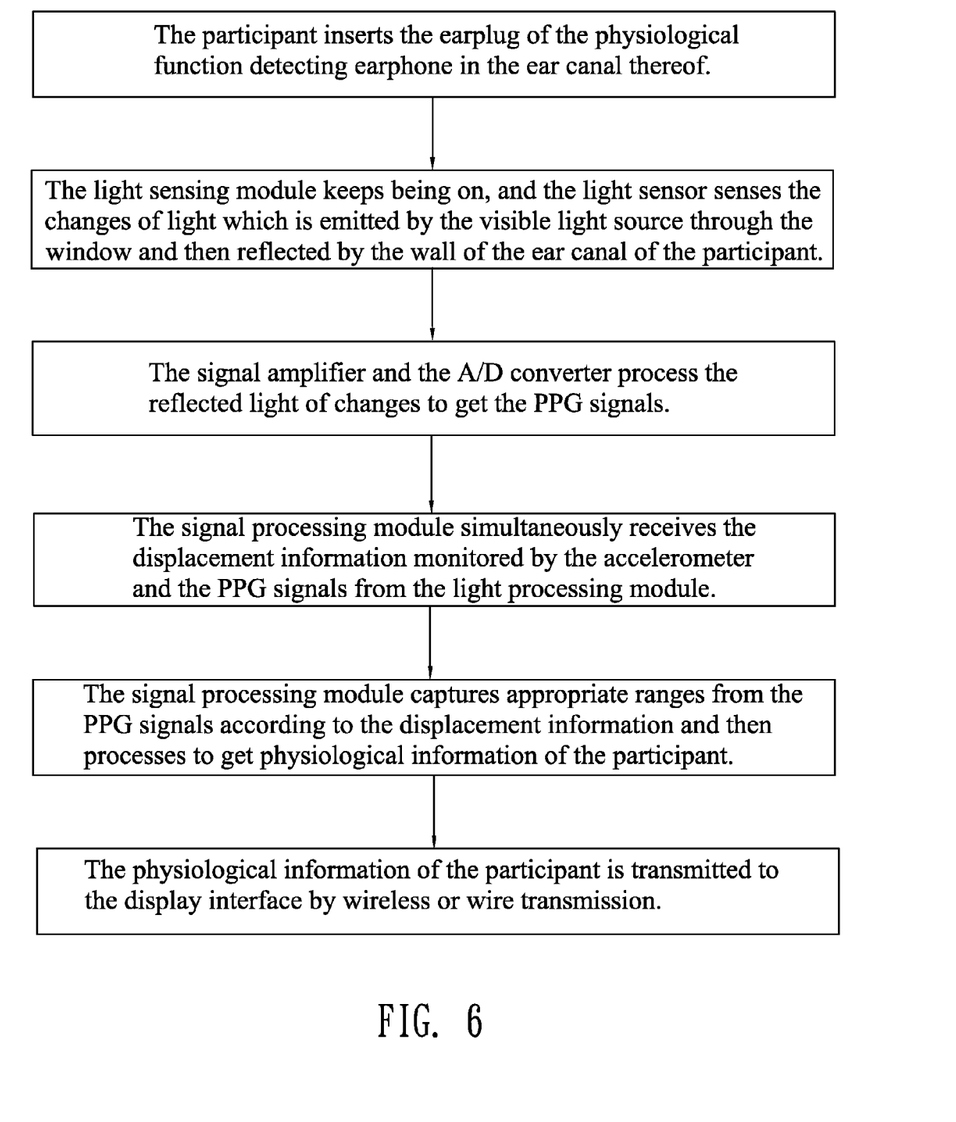

Referring to FIG. 2 and FIG. 6, another detecting method of the physiological function detecting earphone 1 includes the following steps.

Step 1: the participant inserts the earplug 23 of the physiological function detecting earphone 1 in the ear canal thereof.

Step 2: the light sensing module 42 keeps being on, and the light sensor 423 senses the changes of light which is emitted by the visible light source 421 through the window 234 and then reflected by the wall of the ear canal of the participant.

Step 3: the signal amplifier 43 and the A/D converter 44 process the reflected light changes to get the PPG signals.

Step 4: the signal processing module 60 simultaneously receives the displacement information monitored by the accelerometer 50 and the PPG signals from the light processing module 40.

Step 5: the signal processing module 60 captures appropriate ranges from the PPG signals according to the displacement information and then processes to get physiological information of the participant.

Step 6: the physiological information of the participant is transmitted to the display interface 70 by wireless or wire transmission.

In the detecting methods, the signal processing module 60 processes the PPG signals to describe a continuous variation of waveform and then record physiological status of the participant by the HRV analytical method.

As described above, the physiological function detecting earphone 1 according to the present invention utilizes the window 234 opened in the earplug 23 to gather the light in a narrow area of the ear canal of the participant so as to reduce the effect of the manufacturing material on the transmittance of light, and further utilizes the accelerometer 50 to eliminate the effect of the shaking of the participant on the transmittance of light. So the physiological function detecting earphone 1 can effectively improve the accuracy of the PPG signals and the physiological information of the participant.

What is claimed is:

1. A physiological function detecting earphone, comprising:
    an earphone body;
    an earplug mounted at one side of the earphone body, at least one window being opened through the earplug;
    a light processing module including an inner ring spacer, at least one light sensing module disposed on one end face of the inner ring spacer and facing to the at least one window of the earplug, and a signal amplifier and an analog-to-digital (A/D) converter which are disposed on the inner ring spacer and coupled with the at least one light sensing module that includes a visible light source for emitting at least one wavelength of light through the at least one window of the earplug, and a light sensor for sensing reflected light changes by the wall of an ear canal of a participant, the signal amplifier and the A/D converter processing the reflected light changes to get photoplethysmography (PPG) signals; and
    a signal processing module coupled with the signal amplifier and the A/D converter via the inner ring spacer for receiving and processing the PPG signals to obtain the physiological function including at least one of heart rate, heart rate variability (HRV), and degree of blood oxygen saturation of the participant;
    wherein the one side of the earphone body defines a first sound hole of which a circumferentia perpendicularly extends sideward to form a holder, at least one opening is opened through an inside, an outside and a free edge of the holder, a holding frame has a cover board covering an end mouth of the holder, a periphery of the cover board perpendicularly extends to form at least one inserting board made of a material pervious to light and inserted in the at least one opening of the holder, the at least one light sensing module together with a part of the inner ring spacer is located in the holder and faces to the at least one inserting board, the earplug is mounted outside the holder, and the holding frame with the at least one inserting board is exposed through the at least one window; and
    wherein the earplug is made of a lightproof material and has a sleeve worn around the holder and the holding frame, an outer edge of the sleeve extends towards the earphone body to form a substantially bowl-shaped guiding portion, and the at least one window includes a first window and a second window which are in alignment with each other and opened in the sleeve and the guiding portion respectively.

2. The physiological function detecting earphone as claimed in claim 1, wherein the inner ring spacer includes a flexible printed circuit (FPC) board and a connecting frame connected with one end of the FPC board, the FPC board is positioned in the earphone body and the connecting frame is positioned in the earplug, the connecting frame defines at least one fitting surface facing to the window of the earplug, the at least one light sensing module is disposed on the at least one fitting surface, and the signal amplifier and the A/D converter are disposed on the FPC board.

3. The physiological function detecting earphone as claimed in claim 1, wherein the at least one light sensing module further includes an invisible light source disposed in one place with the visible light source and the light sensor, and degree of blood oxygen saturation can be worked out by comparing reflected light signals from the invisible light source with the reflected light signals from the visible light source.

4. The physiological function detecting earphone as claimed in claim 1, wherein the visible light source emits red light at a wavelength of about 610~700 nanometers.

5. The physiological function detecting earphone as claimed in claim 1, wherein an outside of the guiding portion is partly concaved inward to form a groove around the second window.

6. The physiological function detecting earphone as claimed in claim 1, wherein the free edge of the guiding portion perpendicularly protrudes inward to form a light blocking eave, and the sleeve and the light blocking eave abut against the one side of the earphone body.

7. The physiological function detecting earphone as claimed in claim 1, wherein the signal processing module includes a processor and a wireless transmission module, the processor receives the PPG signals and change cycle of the PPG signals and is configured to work out the time interval of each change cycle, then the processor is further configured to describe a continuous variation of waveform and record the physiological function of the participant by an HRV analytical method, and the wireless transmission module transmits the continuous variation of waveform and the physiological function of the participant to a display interface.

8. The physiological function detecting earphone as claimed in claim 7, wherein the signal processing module further includes at least one connector capable of transmitting the continuous variation of waveform and the physiological function of the participant to the display interface.

9. The physiological function detecting earphone as claimed in claim 1, further comprising an accelerometer which is disposed on another end face of the inner ring spacer and faces to another window of the earplug, the accelerometer is coupled with the signal processing module for continuously transmitting displacement information to the signal processing module in use, and the signal processing module judges work start point of the at least one light sensing module and controls on-off states of the at least one light sensing module.

10. A detecting method of using a physiological function detecting earphone, the physiological function detecting earphone comprising an earphone body, an earplug mounted at one side of the earphone body, a light processing module and a signal processing module, and the detecting method comprising the steps of:
   inserting the earplug of the physiological function detecting earphone in an ear canal of a participant, the earplug having at least one window being opened through the earplug;
   using the light processing module to get photoplethysmography (PPG) signals of the participant, the light processing module including an inner ring spacer, at least one light sensing module disposed on one end face of the inner ring spacer and facing to the at least one window of the earplug, and a signal amplifier and an analog-to-digital (A/D) converter which are disposed on the inner ring spacer and coupled with the at least one light sensing module that includes a visible light source for emitting at least one wavelength of light through the at least one window of the earplug, and a light sensor for sensing reflected light changes by the wall of the ear canal of the participant, the signal amplifier and the A/D converter processing the reflected light changes to get the PPG signals; and
   using the signal processing module to couple with the signal amplifier and the A/D converter via the inner ring spacer for receiving and processing the PPG signals to obtain the physiological function including at least one of heart rate, heart rate variability (HRV), and degree of blood oxygen saturation of the participant;
   wherein the one side of the earphone body defines a first sound hole of which a circumferentia perpendicularly extends sideward to form a holder, at least one opening is opened through an inside, an outside and a free edge of the holder, a holding frame has a cover board covering an end mouth of the holder, a periphery of the cover board perpendicularly extends to form at least one inserting board made of a material pervious to light and inserted in the at least one opening of the holder, the at least one light sensing module together with a part of the inner ring spacer is located in the holder and faces to the at least one inserting board, the earplug is mounted outside the holder, and the holding frame with the at least one inserting board is exposed through the at least one window; and
   wherein the earplug is made of a lightproof material and has a sleeve worn around the holder and the holding frame, an outer edge of the sleeve extends towards the earphone body to form a substantially bowl-shaped guiding portion, and the at least one window includes a first window and a second window which are in alignment with each other and opened in the sleeve and the guiding portion respectively.

11. The detecting method as claimed in claim 10, wherein the physiological function detecting earphone further comprises an accelerometer which is disposed on another end face of the inner ring spacer and faces to another window of the earplug, and after the earplug is inserted in the ear canal of the participant, the signal processing module receives displacement information monitored by the accelerometer and then controls on-off states of the at least one light sensing module according to the displacement information.

12. The detecting method as claimed in claim 10, wherein the physiological function detecting earphone further comprises an accelerometer which is disposed on another end face of the inner ring spacer and faces to another window of the earplug, and after the earplug is inserted in the ear canal of the participant, the signal processing module simultaneously receives displacement information monitored by the accelerometer and the PPG signals from the light processing module, then the signal processing module captures ranges from the PPG signals according to the displacement information and processes the PPG signals of the participant.

13. The detecting method as claimed in claim 10, wherein the signal processing module processes the PPG signals to describe a continuous variation of waveform and then record the physiological function of the participant by an HRV analytical method.

* * * * *